US012357654B2

(12) United States Patent
Yang et al.

(10) Patent No.: US 12,357,654 B2
(45) Date of Patent: Jul. 15, 2025

(54) APPLICATION OF GLUCAN IN PREPARATION OF DRUG

(71) Applicants: Qingdao Conson Pharmaceutical Co., Ltd., Shandong (CN); Marine Biomedical Research Institute of Qingdao Co., Ltd., Shandong (CN)

(72) Inventors: Jinbo Yang, Shandong (CN); Guangli Yu, Shandong (CN); Qiaoling Song, Shandong (CN); Lijuan Wu, Shandong (CN); Jun Zhao, Shandong (CN); Youjing Lv, Shandong (CN); Chenyang Zhao, Shandong (CN); Huashi Guan, Shandong (CN)

(73) Assignees: QINGDAO CONSON PHARMACEUTICAL CO., LTD., Shandong (CN); MARINE BIOMEDICAL RESEARCH INSTITUTE OF QINGDAO CO., LTD., Shandong (CN)

( * ) Notice: Subject to any disclaimer, the term of this patent is extended or adjusted under 35 U.S.C. 154(b) by 716 days.

(21) Appl. No.: 17/618,311

(22) PCT Filed: Jun. 15, 2020

(86) PCT No.: PCT/CN2020/096223
§ 371 (c)(1),
(2) Date: Dec. 10, 2021

(87) PCT Pub. No.: WO2020/249132
PCT Pub. Date: Dec. 17, 2020

(65) Prior Publication Data
US 2022/0331352 A1 Oct. 20, 2022

(30) Foreign Application Priority Data
Jun. 13, 2019 (CN) .......................... 201910512814.6

(51) Int. Cl.
*A61K 31/716* (2006.01)
*A61K 45/06* (2006.01)
(Continued)

(52) U.S. Cl.
CPC ............ *A61K 31/716* (2013.01); *A61K 45/06* (2013.01); *A61P 7/00* (2018.01); *A61P 35/00* (2018.01); *A61P 37/04* (2018.01)

(58) Field of Classification Search
CPC .... A61K 31/716; A61K 45/06; A61K 31/555; A61K 39/395; A61K 36/03;
(Continued)

(56) References Cited

U.S. PATENT DOCUMENTS 10,912,794 B2  2/2021  Horst et al.

FOREIGN PATENT DOCUMENTS

CN  101020719 A  8/2007
CN  105001352 A  10/2015
(Continued)

OTHER PUBLICATIONS

Orecchioni et al. Vinorelbine, cyclophosphamide and 5-FU effects on the circulating and intratumoural landscape of immune cells improve anti-PD-L1 efficacy in preclinical models of breast cancer and lymphoma (BJC, 2018, 118, 1329-1336). (Year: 2018).*
(Continued)

*Primary Examiner* — Scarlett Y Goon
*Assistant Examiner* — Sarah Grace Scrivener
(74) *Attorney, Agent, or Firm* — Panitch Schwarze Belisario & Nadel LLP (57) ABSTRACT

An application of a glucan in the preparation of a drug. A β-1,3/1,6-glucan is used for preparing a pharmaceutical composition or formulation. The pharmaceutical composition or formulation can enhance the antitumor effect of
(Continued)

immunotherapy, radiotherapy, or chemotherapy, and is used for treating leukopenia and/or thrombocytopenia.

13 Claims, 10 Drawing Sheets

(51) Int. Cl.
    *A61P 7/00*     (2006.01)
    *A61P 35/00*     (2006.01)
    *A61P 37/04*     (2006.01)

(58) Field of Classification Search
    CPC ...... A61K 2039/505; A61P 7/00; A61P 35/00; A61P 37/04; A61P 7/02; Y02A 50/30; C07K 16/2818
    See application file for complete search history.

(56) References Cited

FOREIGN PATENT DOCUMENTS

| | | |
|---|---|---|
| CN | 108430479 A | 8/2018 |
| CN | 109793752 A | 5/2019 |
| JP | H8500623 A | 1/1996 |
| JP | 2017535543 A | 11/2017 |
| WO | 9404163 A1 | 3/1994 |
| WO | 2004014320 A2 | 2/2004 |
| WO | 2016073763 A2 | 5/2016 |

OTHER PUBLICATIONS

Bobadilla et al., "Soluble Beta-1,3/1,6-glucan in seaweed from the southern hemisphere and its immunomodulatory effect," Carbohydrate Polymers, vol. 92, pp. 241-248 (2013).
Camilli et al., "The Complexity of Fungal beta-Glucan in Health and Disease: Effects on the Mononuclear Phagocyte System," Front Immunol., vol. 9, No. 673, pp. 1-9 (2018).
Kim et al., "Immune escape tp PD-L1/PD-1 blockade: seven steps to success," Annals of Oncology, vol. 27, pp. 1492-1504 (2016).
Mahoney et al., "Combination cancer immunotherapy and new immunomodulatory targets," Nat. Rev. Drug Discov., vol. 14, No. 8, pp. 561-584 (2015).
Wang et al., "Structural characterization and immuno-enhancing activity of a highly branched water-soluble beta-glucan from the spores of Ganoderma lucidum," Carbohydrate Polymers, vol. 167, pp. 337-344 (2017).
Wu et al., "Advances in the study of immunomodulatory effects of beta-glucan," Chin. J. Cell Mol. Immunol., vol. 30, No. 1, pp. 97-100 (2014) (with machine English translation of Abstract).
Zhang et al., "Optimizing Tumor Microenvironment for Cancer Immunotherapy: Beta-Glucan-Based Nanoparticles," Frontiers in Immunolgy, vol. 9, No. 341, pp. 1-14 (2018).
Office Action issued Jan. 4, 2023 in JP Application No. 2021574203 (English translation).
Office Action issued Jan. 13, 2023 in CA Application No. 3143308.
Extended European Search Report issued Jun. 9, 2023 in EP Application No. 20822937.7.
Office Action issued Dec. 12, 2022 in AU Application No. 2020291757.
Office Action issued Jul. 28, 2022 in CN Application No. 202080043041.2 (English translation).
Office Action issued Feb. 22, 2023 in CN Application No. 202080043041.2.
Karaca et al., "Positive Effects of Oral b-Glucan on Mucositis and Leukopenia in Colorectal Cancer Patients Receiving Adjuvant Folfox-4 Combination Chemotherapy," Asian Pacific Journal of Cancer Prevention, vol. 15, No. 8, pp. 3641-3644 (2014).
Ghareeb et al., "Concomitant treatment with beta-glucan and G-CSF ameliorates altered biochemical indices after cyclophosphamide-induced leukopenia in mice," Biotechnology & Biotechnological Equipment, vol. 29, No. 5., pp. 970-976 (2015).
Su et al., "A b-1,3/1,6-glucan from Durvillaea Antarctica inhibits tumor progression in vivo as an immune stimulator," Carbohydrate Polymers, vol. 222, 114993, pp. 1-11 (2019).
Chae et al., "Yeast (1-3)-(1-6)-b-D-glucan alleviates immunosuppression in gemcitabine-treated mice," International Journal of Biological Macromolecules, vol. 136, pp. 1169-1175 (2019).
Yang et al., "A b-glucan from Durvillaea Antarctica has immunomodulatory effects on RAW264.7 macrophages via toll-like receptor 4," Carbohydrate Polymers, vol. 191, pp. 255-265 (2018).

\* cited by examiner

APPLICATION OF GLUCAN IN PREPARATION OF DRUG

CROSS-REFERENCE TO RELATED APPLICATIONS

This application is a Section 371 of International Application No. PCT/CN2020/096223, filed Jun. 15, 2020, which was published in the Chinese language on Dec. 17, 2020, under International Publication No. WO 2020/249132 A1, which claims priority under 35 U.S.C. § 119 (b) to Chinese Application No. 201910512814.6 filed Jun. 13, 2019, the disclosure of each of which is incorporated herein by reference in its entirety.

TECHNICAL FIELD

The present invention relates to the field of marine pharmaceuticals, and specifically to the application of a β-1,3/1,6-glucan, the β-1,3/1,6-glucan is used in the preparation of pharmaceutical compositions or formulations that can be used for enhancing the antitumor effect of immunotherapy, radiotherapy, or chemotherapy, and for the treatment of leukocytopenia and/or thrombocytopenia.

BACKGROUND

β-glucans are long-chain polysaccharides composed of glucose from the cell walls of fungi, yeast, certain bacteria and plants. The main chains of these polymers contain linear β-D-(1,3) glucosyl units which are substituted with side chains linked by β-D-(1,6) glucosyl units at O-6 site varying in molecular weight size and distribution.

3-glucans are thought to be pathogen-associated molecular patterns (PAMPs) that regulate host immune responses by triggering innate immune cells such as neutrophils, macrophages and granulocytes. At present, most of the β-1,3-glucan in the market derived from barley, oats, edible fungi (*Shiitake, Grifola frondosa, Schizophyllum*), yeast and other terrestrial organisms. The molecular weight, linkage and degree of branch of the obtained β-1,3-glucan vary greatly due to different sources of raw materials, and it is difficult to control the quality, for example, the β-glucan for injection medicine mainly comes from shiitake, a kind of β-1,3-glucan with β-1,6-branches, having poor soluble in water due to its high molecular weight of 400-800 kDa.

Cancer immunotherapy, treating cancer by exogenously stimulating the immune system, has become a promising strategy for cancer treatment. For example, inhibitors for immune checkpoints such as cytotoxic T-lymphocyte antigen 4 (CTLA4), programmed cell death receptor 1 (PD-1) and its ligand (PD-L1) have achieved great success in a variety of cancers by blocking immunosuppressive signals and enhancing the autonomic antitumor response.

Cancer immunotherapies targeting PD-1 achieved great success by modulating the immune environment to elicit more effective antitumor response. However, only a part of patients will benefit from drug alone for PD-1 blockade. Chemoradiotherapy is the most commonly used cancer treatment, but due to the high toxicity and other features of chemoradiotherapy, patients with cancer may undergo various degrees of side effects during the chemoradiotherapy, the most common of which may be causing leukocytopenia and leading to life-threatening infections.

SUMMARY OF INVENTION

The purpose of the present invention is to provide a use of β-1,3/L6-glucan, including anti-tumor, increasing leukocytes and resistance to thrombocytopenia, and the β-1,3/1,6-glucan has the characteristics of good water solubility and high safety.

The first aspect of the present invention provided is a use of β-1,3/1,6-glucan, characterized in that the β-1,3/1,6-glucan is derived from Antarctic brown algae, the β-1,3/1,6-glucan is used in the preparation of a pharmaceutical composition or preparation, and the pharmaceutical composition or formulation is used for the treatment of leukopenia and/or thrombocytopenia.

In another preferred embodiment, the H1 signal in 1H-NMR of the β-1,3/1,6-glucan locates in an area of 4.40-4.64 ppm, and the Cl signal in 13C-NMR is locates in an area of 102.4-102.67 ppm.

In another preferred embodiment, the Antarctic brown algae is Cochayuyo, sea bamboo shoot or *Lessonia trabeculata*, or *Durvillaea antarctica*.

In another preferred embodiment, the β-1,3/1,6-glucan is a β-glucan of formula (I) and/or formula (II), wherein n is an integer selected from 1-20 (e.g., 1, 2, 3, 4, 5, 6, 7, 8, 9, 10, 11, 12, 13, 14, 15, 16, 17, 18, 19 or 20), and R is H and/or no more than 4 glucose residues (e.g., 1, 2, 3 or 4 glucose residues).

In another preferred embodiment, R in the structure of formula (I) or formula (II) is one or more of the structures of formula (III) or formula (IV) or formula (V) or formula (VI), wherein formula (III): Glcβ1-;

formula (IV): Glcβ1-3Glcβ1- or Glcβ1-6Glcβ1-;

formula (V): Glcβ1-3Glcβ1-3Glcβ1-, or Glcβ1-6Glcβ1-3Glcβ1-, or

Glcβ1-3Glcβ1-6Glcβ1-, or Glcβ1-6Glcβ1-6Glcβ1-;

Formula (VI):
  Glcβ1-3Glcβ1-3Glcβ1-3Glcβ1- or
  Glcβ1-6Glcβ1-3Glcβ1-3Glcβ1- or
  Glcβ1-3Glcβ1-6Glcβ1-3Glcβ1- or
  Glcβ1-3Glcβ1-3Glcβ1-6Glcβ1- or
  Glcβ1-6Glcβ1-6Glcβ1-3Glcβ1- or
  Glcβ1-6Glcβ1-3Glcβ1-6Glcβ1- or
  Glcβ1-3Glcβ1-6Glcβ1-6Glcβ1- or
  Glcβ1-6Glcβ1-6Glcβ1-6Glcβ-.

In another preferred embodiment, the molecular weight of the β-1,3/1,6-glucan is 1-50 kDa; preferably, 2-30 kDa; more preferably, 2-10 kDa; most preferably is 4-7 kDa.

In another preferred embodiment, the specific rotation of the β-1,3/1,6-glucan is not less than −15.0°; preferably, −15° to 25°; more preferably, −15° to −21°.

In another preferred embodiment, the UV full-wavelength scanning pattern of the β-1,3/1,6-glucan has no obvious absorption in the wavelength range of 300 to 900 nm; more preferably, no obvious absorption in the wavelength range of 230 to 900 nm.

In another preferred embodiment, the UV full wavelength scan spectrum of the β-1,3/1,6-glucan has no absorption peak in the wavelength range of 260~280 nm. In another preferred embodiment, the side chain length of the β-1,3/1,6-glucan is ≤5.

In another preferred embodiment, the β-1,3/1,6-glucan can be prepared by the following steps:

(1) degreasing: drying and smashing Antarctic brown algae, then soaking in organic solvent and stirring to obtain a degreased algal powder;

(2) aqueous extraction: extracting the degreased algae powder by stirring with water at room temperature to obtain an aqueous extract;

(3) grading: centrifuging the aqueous extract obtained from step (2), adding aqueous solution of 1-3 mol/L calcium chloride to the supernatant obtained from centrifugation; centrifuging after stirring, taking the supernatant for dialysis or ultra-filtration desalination, concentrating under reduced pressure and drying to obtain crude polysaccharide;

(4) purification: dissolving the crude polysaccharide from step (3) in distilled water, separating and purifying through anion exchange resin with distilled water and aqueous sodium chloride solution as the mobile phase, collecting the aqueous elution fraction, concentrating under reduced pressure and lyophilizing to obtain the β-1,3/1,6-glucan.

In another preferred embodiment, the purification of step (4) is: dissolving the crude polysaccharide from step (3) in distilled water, separating and purifying through anion exchange resin with distilled water and aqueous sodium chloride as mobile phases, and detecting using sulfuric acid phenol method, collecting the aqueous elution fraction, concentrating under reduced pressure, and lyophilizing to obtain the β-1,3/1,6-glucan.

In another preferred embodiment, the separation and purification with anion resin is separating and purifying through strong anion ion resin.

In another preferred embodiment, the separation and purification with anion resin is: firstly, separating and purifying through a strong anion resin, and then separating and purifying through a weak anion resin; or separating and purifying through a weak anion ion resin, and then separating and purifying through a strong anion ion resin.

In another preferred embodiment, the strong anion resin is an anion resin containing quaternary ammonium groups.

In another preferred embodiment, the weak anion resin is an anion resin containing diethylaminoethyl.

In another preferred embodiment, the invention provided is a use of β-1,3/1,6-glucan, wherein the leukocytes are lymphocytes.

In another preferred embodiment, the lymphocytes are B cells and/or T cells.

In another preferred embodiment, the use of the β-1,3/1,6-glucan is characterized in that the pharmaceutical composition or preparation further has an effect of anti-tumor.

In another preferred embodiment, the use of the β-1,3/1,6-glucan is characterized in that the pharmaceutical composition or preparation can further be used in combination with immune checkpoint drugs.

In another preferred embodiment, the use of β-1,3/1,6-glucan is characterized in that the immune checkpoint drug is selected from programmed death 1 protein (PD-1) antagonist, or a PD-L1 antagonist, or a cytotoxic T lymphocyte antigen (CTLA-4) antagonist, or a lymphocyte activation gene-3 (LAG-3) antagonist, or a T cell immunoglobulin-3 (TIM-3) antagonist, or T-cell immunoglobulin and ITIM structural domain protein (TIGIT) antagonist.

In another preferred embodiment, the use of β-1,3/1,6-glucan is characterized in that the immune checkpoint drug is selected from the group consisting of anti-PD-1 antibody, and anti-PD-L1 antibody.

In another preferred embodiment, the use of the β-1,3/1,6-glucan in the preparation of drugs for treatment of leukocytopenia and/or thrombocytopenia is characterized in that the anti-PD-1 antibody or PD-L1 antibody is selected from Durvalumab, Atezolizumab, Nivolumab, BMS202, Spartalizumab, and Camrelizumab.

In another preferred embodiment, the combination use of the pharmaceutical composition or preparation and the programmed death 1 protein (PD-1) or PD-L1 antagonist is administered simultaneously, sequentially or separately.

In another preferred embodiment, the use of the β-1,3/1,6-glucan is characterized in that the pharmaceutical composition or preparation can further be used in combination with at least one chemotherapeutic agent.

In another preferred embodiment, the use of the β-1,3/1,6-glucan is characterized in that the chemotherapeutic agent is selected from cytotoxic chemotherapeutic agents.

In another preferred embodiment, the use of β-1,3/1,6-glucan is characterized in that the chemotherapeutic agent is selected from one of anthracyclines, 5-Fus, and alkaloids.

In another preferred embodiment, the use of β-1,3/1,6-glucan is characterized in that the chemotherapeutic agent is selected from one of cisplatin and carboplatin.

In another preferred embodiment, the use of the β-1,3/1,6-glucan, the combination use of the pharmaceutical composition or preparation and the chemotherapeutic agent is administered simultaneously, sequentially or separately.

In another preferred embodiment, the use of the β-1,3/1,6-glucan is characterized in that the pharmaceutical composition or preparation can further be used in combination with radiotherapy.

In another preferred embodiment, the use of the β-1,3/1,6-glucan, the combination use of the pharmaceutical composition or preparation and the radiotherapy is administered simultaneously, sequentially or separately.

In another preferred embodiment, the use of the β-1,3/1,6-glucan is characterized in that the pharmaceutical composition or preparation is used for treatment of cancer in a subject.

In another preferred embodiment, the cancer is one or more of melanoma, colorectal cancer, lung cancer, kidney cancer, liver cancer and breast cancer.

In another preferred embodiment, the pharmaceutical composition or preparation comprises a safe and effective amount of β-1,3/1,6-glucan, and pharmaceutically acceptable carriers or excipients.

It should be understood that within the scope of the present invention, the above-described technical features of the present invention and the technical features described in detail below (e.g., embodiments) may be combined with each other to constitute a new or preferred technical solution. Limited by space, it will not be repeated here.

DETAILED DESCRIPTION OF THE INVENTION

Terms

Unless otherwise defined, the following terms used in the specification and claims have the meanings commonly understood by those skilled in the art. Unless otherwise stated, all patents, applications, and published materials cited throughout this document are incorporated herein by reference in their entirety. As used in the present invention, PLT, platelet count; NEUT, neutrophils; LYMPH, lymphocytes; MONO, monocytes; WBC, white blood cells.

In the present invention, the terms "strong anion resin" and "strong anion exchange resin" are used interchangeably, to referring to anion resins containing strong reactive groups such as quaternary amine groups.

In the present invention, the terms "weak anion resin" and "weak anion exchange resin" are used interchangeably, referring to anion resins containing weaker reactive groups such as diethylaminoethyl.

The main advantages of the invention include:

(1) The β-1,3/1,6-glucan described in the present invention, derived from marine Antarctic brown algae, is characterized by small molecular weight, good water solubility and high safety, and has the effect of resisting leukocyte reduction and thrombocytopenia, especially having good effects on the reduction of T-lymphocyte and B-lymphocyte caused by tumor treatment.

The present invention is further elaborated below in conjunction with specific embodiments, and other advantages and features of the present invention will become clearer after reading the specific embodiments of the present invention in conjunction with the accompanying drawings. It should be understood that these embodiments are only used to illustrate the present invention and not to limit the scope of the present invention. In the following examples, the test methods without specific conditions are usually in accordance with conventional conditions or the conditions recommended by the manufacturer.

Example 1. Effect of β-1,3/1,6-Glucan in Combination with Anti-PD-1 Antibody in B16 Syngeneic Tumor Model A cell suspension of $3 \times 10^5$ mouse melanoma cell line B16 (presented by PerkinElmer) was injected subcutaneously into C57BL/6J mice (female, 6-8 weeks old, purchased from Jinan Pengyue Experimental Animal Company). The administration experiments were performed about 4 days after implantation when B16 tumors have grown to be palpable. Mice were divided into four groups and treated with vehicle or β-1,3/1,6-glucan (4 mg/kg, i.v., twice a week) alone, or in combination with anti-PD-1 antibody (anti-mouse PD-1 antibody purchased from BioxCell, 200 μg per mouse, i.v., once a week). Tumor volumes were evaluated and tumor weights were recorded. After sacrifice of mice, blood and tumor samples were collected for flow cytometric analysis.

Blood samples were collected by cardiac puncture, collected into EDTA-anticoagulation tubes. 50 μl of whole blood was taken for blood analysis, 50 μl of whole blood was taken for erythrocyte lysis (erythrocyte lysis buffer, Meltenyi), and the remaining whole blood was centrifuged at 3500 rpm for 7 min and the plasma was taken and stored at −80° C. Spleens and thymus were weighed for recording. Subcutaneous tumors of mice, about 0.2-0.5 g of tumors tissues, were taken, and single cell suspensions from the tumor samples were obtained by Mouse Tumor Dissociation Kit (Meltenyi). The blood cells after erythrocyte lysis as well as the dissociated tumor cell suspensions were subjected to subsequent processing, as well as flow cytometric detection The single-cell suspensions were blocked with blocking buffer (20% FBS, 1:100 CD16/CD32 antibody and 1:100 rat IgG) for 20 min, and incubated and stained with the corresponding immune cell surface protein antibodies (CD11 b-PE, CD4-BV510, CD8-PerCP-Cy5.5, CD19-APC, CD3-FITC, CD206-PE-Cy7, Ly6C-APC) for 30 minutes at 4° C. Analysis of immune cell population ratios was performed by FACS Arial III (BD Biosciences). The specific procedure was delineating the cell population in the FSC/SSC quadrant, delineating single cell population by FSC-H and FSC-A, and delineating corresponding immune cells by immune cell surface markers, and calculating the cell ratio or relative concentration.

Figure 1:
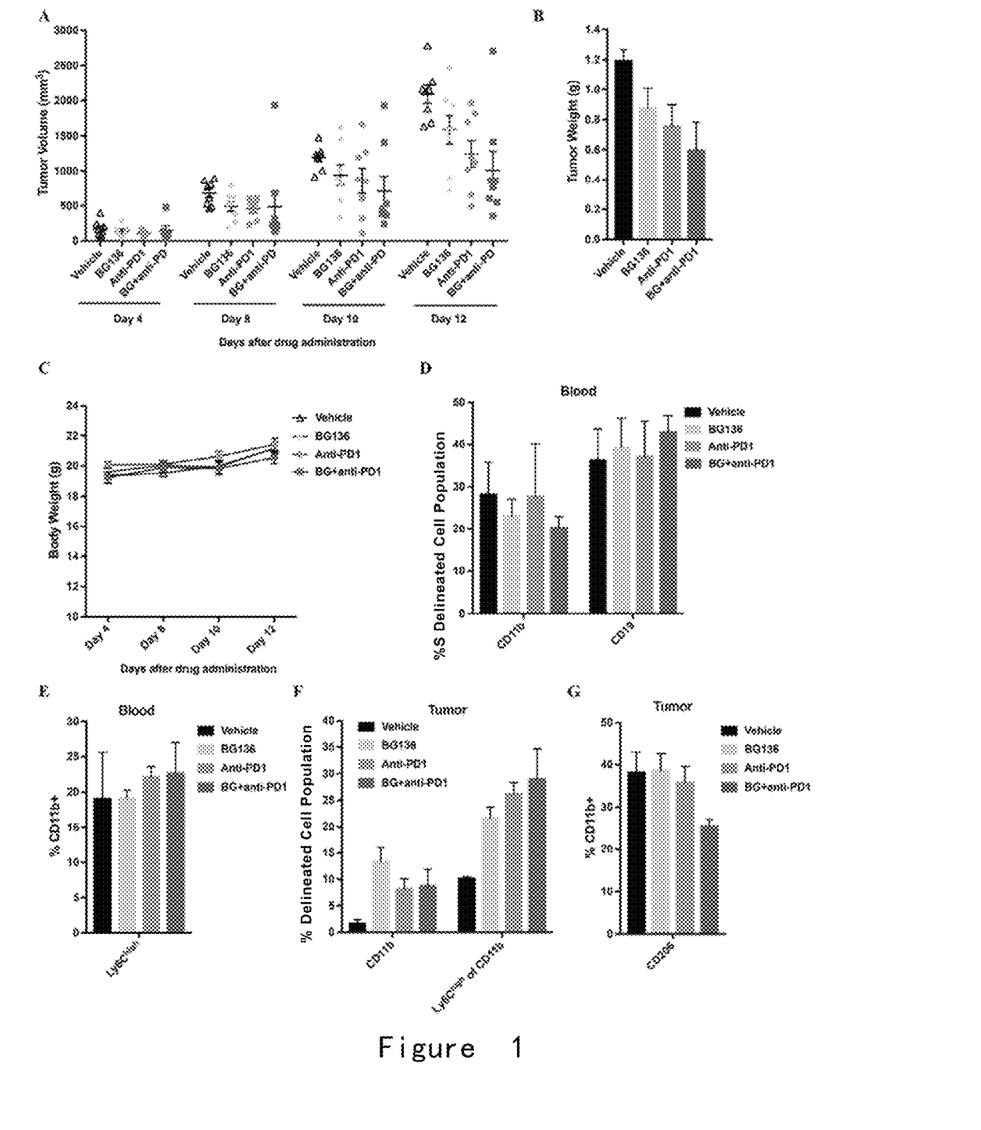
FIG. 1 shows the effect of β-1,3/1,6-glucan in combination with anti-PD-1 antibody on B16 syngeneic tumor model.
Figure 2:
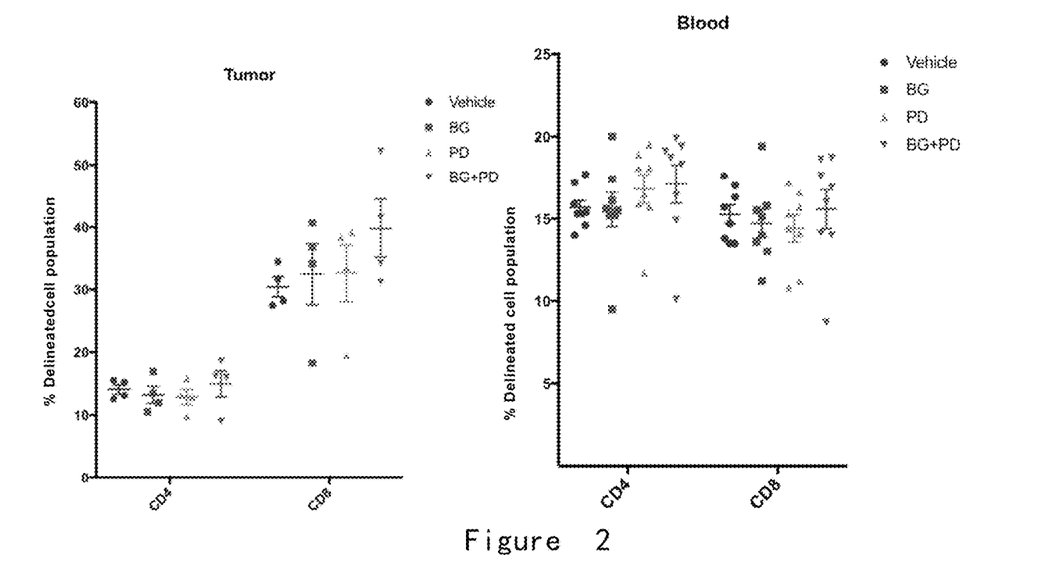
FIG. 2 shows the effect of β-1,3/1,6-glucan in combination with anti-PD-1 antibody on T lymphocytes in the B16 syngeneic tumor model.

As shown in FIGS. 1A and 1B, B16 syngeneic tumor mice were treated with vehicle, β-1,3/1,6-glucan (4 mg/kg, i.v., twice a week), anti-PD-1 antibody (200 μg/mouse, i.v., once a week), or a combination of β-1,3/1,6-glucan and anti-PD-1 antibody (dosing started on day 4; the vehicle group, the combination group and single groups of β-1,3/1,6-glucan and PD-1 were dosed via tail vein injection on day 4; the vehicle group and PD-1 group were dosed vehicle, and β-1,3/1,6-glucan group and the combination group of β-1, 3/1,6-glucan and PD-1 were administrated β-1,3/1,6-glucan on day 7 the administration on day 10 was as the same on day 4, and the administration on day 13 was the same as on day 7), the tumor volume was assessed during the administration, the mice were sacrificed on day 14 and tumor weight and other indices were assessed. The results showed that β-1,3/1,6-glucan enhances anti-PD-1 antibody-induced tumor regression in B16 syngeneic tumor model, and the combination thereof with anti-PD-1 antibody more effectively inhibits tumor growth than single treatment. There were no significant changes in body weight and death of mice during treatment, indicating that the combination therapy did not cause any serious toxicity (FIG. 1C). Analysis of immune cell subpopulations in blood and tumors by flow cytometer showed that the combination treatment increases the percentage of CD19+ cells and decreases the percentage of CD11b+ cells in the blood of mice (FIG. 1D). Combination treatment also upregulates pro-inflammatory monocyte-derived macrophages (CD11b+Ly6Chi, FIG. 1E) in the peripheral blood. Detection of tumor-infiltrating immune cells showed that within the tumor, more infiltration of myeloid cells (CD11 b+), especially pro-inflammatory macrophages (CD11b+Ly6Chi) (FIG. 1F), and the percentage of immunosuppressive tumor-associated macrophages TAM (CD11b+CD206+) is also reduced after the combination treatment compared with anti-PD-1 antibody treatment alone (FIG. 1G). In addition, it was detected that the combination application of β-1,3/1,6-glucan and PD-1 antibodies enhances the percentage of CD4 and CD8 T cells in the blood and tumor (FIG. 2). It was shown that β-1,3/1,6-glucan and anti-PD-1 antibodies synergistically increase tumor infiltration of pro-inflammatory macrophages, decrease the percentage of immunosuppressive TAM, and increase the ratio of acquired immune cells T and B cells, resulting in building up a more pro-inflammatory and anti-tumoral tumor microenvironment.

Figure 3:
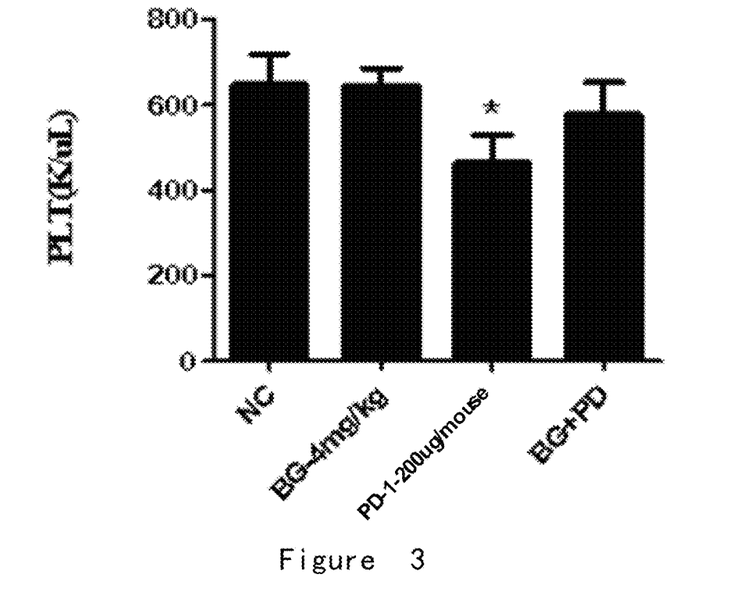
FIG. 3 shows the effect of β-1,3/1,6-glucan in combination with anti-PD-1 antibody on platelets in the B16 syngeneic tumor model.

Example 2. Effect of β-1,3/1,6-Glucan in Combination with Anti-PD-1 Antibody on Platelets in the B16 Syngeneic Tumor Model The experimental method was the same as in Example 1. On day 14, blood was taken from the heart after animal sacrificed, placed in EDTA-anticoagulation tubes. After mixing, 50 μl was taken and platelet concentration was measured by a hematology analyzer. As shown in FIG. 3, PD-1 antibody alone reduces platelet concentration, and β-1,3/1,6-glucan alone does not affect platelet concentration, while the combination thereof with PD-1 antibody reverses the platelet-lowering side effect of PD-1 antibody.

Example 3. Effect of the Combination of β-1,3/1,6-Glucan and Anti-PD-1 Antibody on the Number of Lymphocytes in Peripheral Blood The experimental method was the same as in Example 1. On day 14, blood was taken from the heart after animal sacrificed, and placed in EDTA-anticoagulation tubes. After mixing, 50 μl of whole blood was taken. 5 μl of GFP microspheres were added to each sample for erythrocyte lysis.

The single-cell suspensions were blocked with blocking buffer (20% FBS, 1:100 CD16/CD32 antibody and 1:100 rat IgG) for 20 min, and incubated and staining with the corresponding immune cell surface protein antibodies (CD4-BV510, CD8-PerCP-Cy5.5, CD19-APC, CD3-FITC) for 30 minutes at 4° C. Analysis of immune cell population ratios was performed by FACS Arial III (BD Biosciences).

The specific procedure was delineating the cell population in the FSC/SSC quadrant, delineating the single cell population by FSC-H and FSC-A, and delineating the corresponding immune cells by immune cell surface markers, and calculating the relative immune cell concentration.

Figure 4:
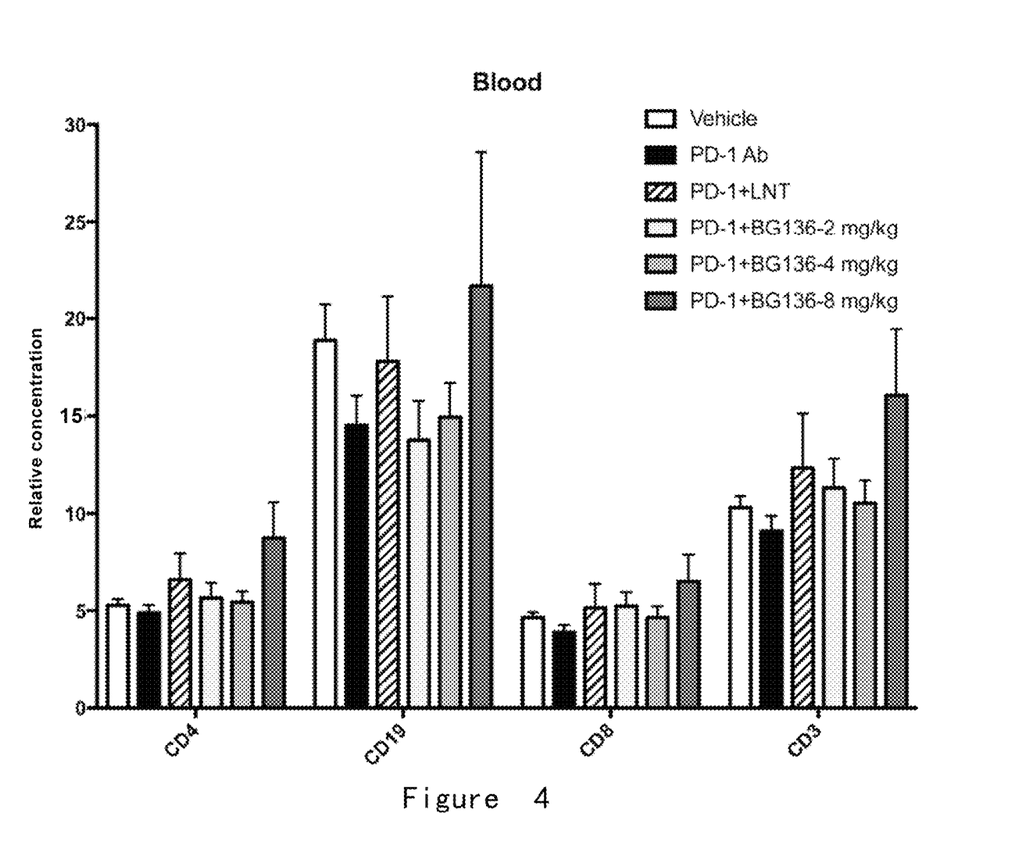
FIG. 4 shows the effect of β-1,3/1,6-glucan in combination with anti-PD-1 antibody on lymphocytes in the B16 syngeneic tumor model.

The experimental results in FIG. 4 showed that PD-1 antibody alone can increase the relative concentrations of CD3, CD4 and CD8 in blood, while the combination of 8 mg/kg β-1,3/1,6-glucan and PD-1 antibody can further increase the relative concentrations of CD3, CD4, CD8 and CD19 in blood, indicating that β-1,3/1,6-glucan can further enhance the immune activating effect of PD-1 antibody.

Example 4. Application of β-1,3/1,6-Glucan to a Mouse Model after Radiotherapy

A cell suspension of $3 \times 10^5$ mouse melanoma cell line B16 (presented by PerkinElmer) was injected subcutaneously into C57BL/6J mice (female, 6-8 weeks old, purchased from Jinan Pengyue Experimental Animal Company)(Overwijk & Restifo, 2001). About 5 days after tumor implantation, local radiotherapy (tumor injection area, 10 Gy) was applied. On day 6 and day 14, vehicle or β-1,3/1,6-glucan was administered (tail vein injection, once a week), during this period, tumor volume and mouse body weight were measured, and on day 17, after the animals were sacrificed, tumor weight was measured.

Figure 5:
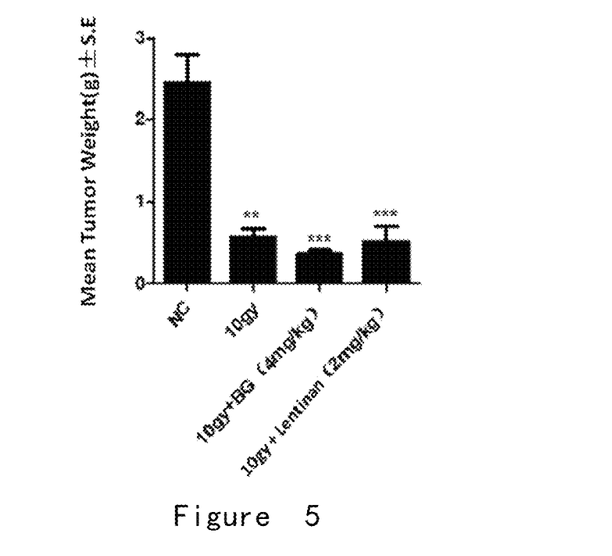
FIGS. 5-7 show the antitumor effect of β-1,3/1,6-glucan in combination with radiotherapy on B16 syngeneic tumor model.
Figure 6:
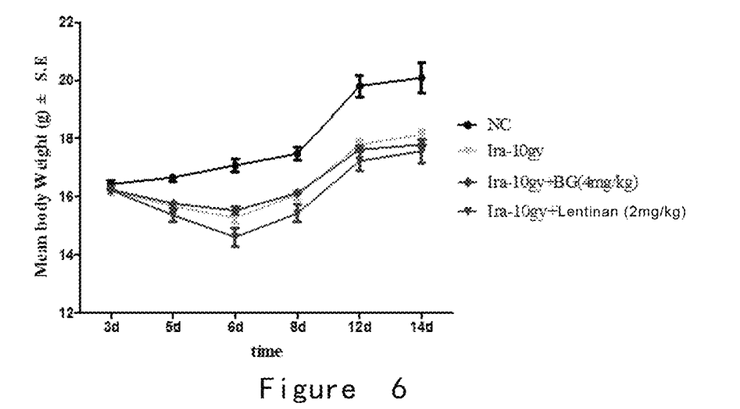
Figure 7:
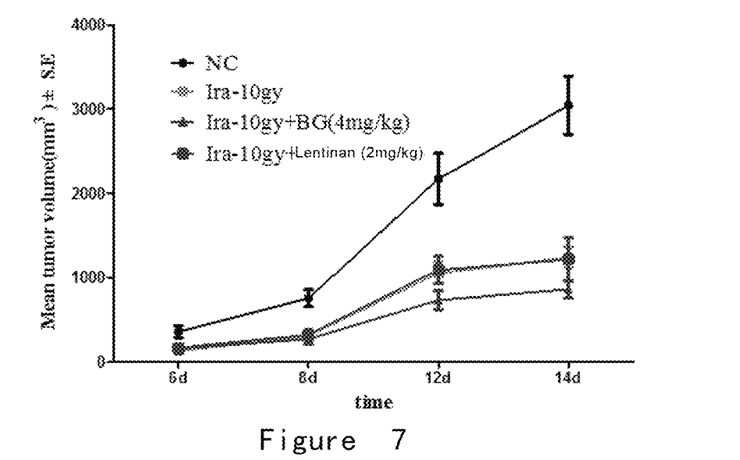
Figure 8:
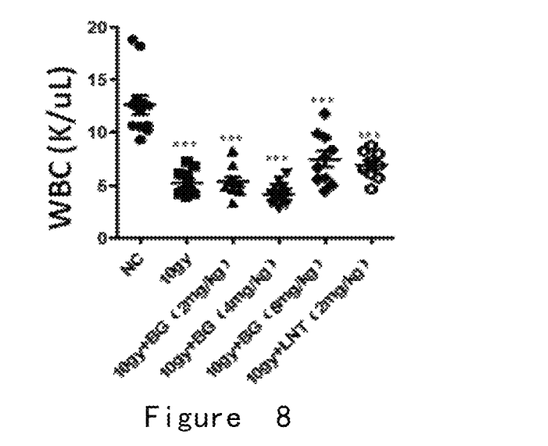
FIGS. 8-15 show the effect of β-1,3/1,6-glucan in combination with radiotherapy on leukocytes in the B16 syngeneic tumor model.
Figure 9:
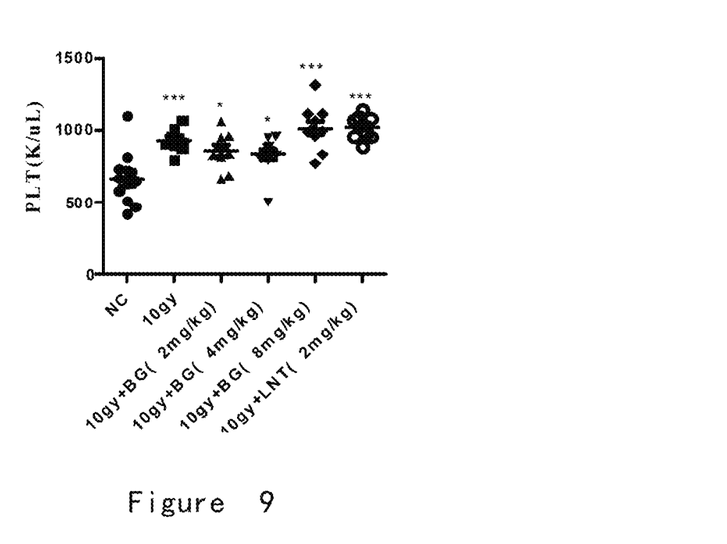
Figure 10:
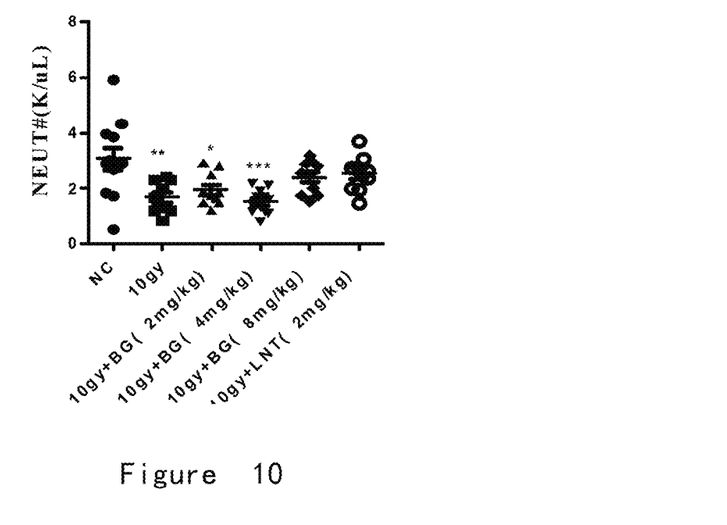
Figure 11:
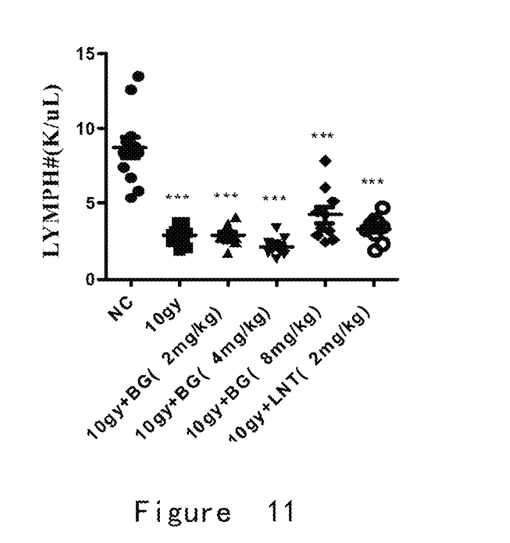
Figure 12:
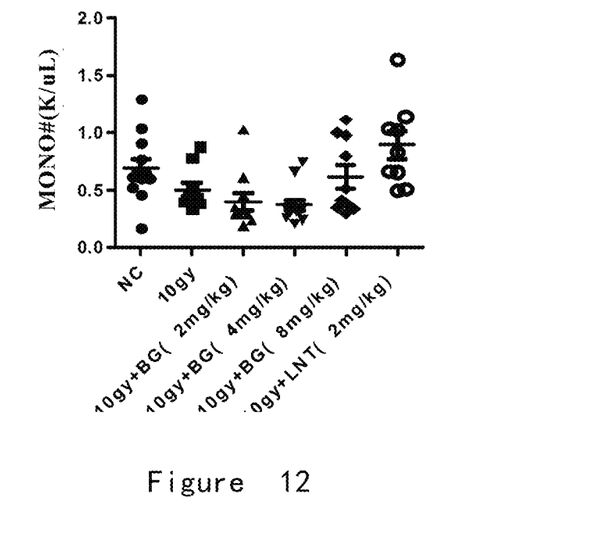
Figure 13:
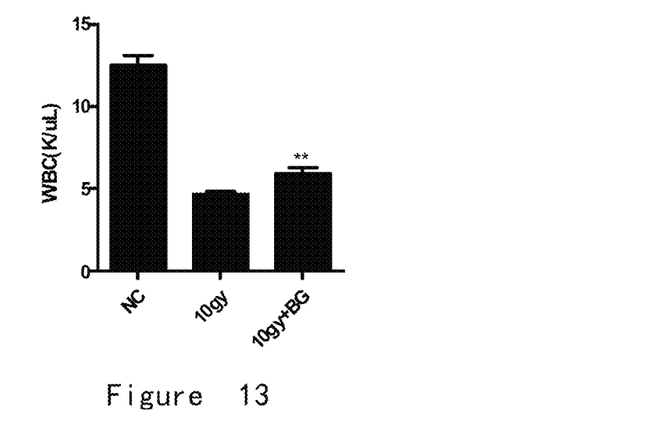
Figure 14:
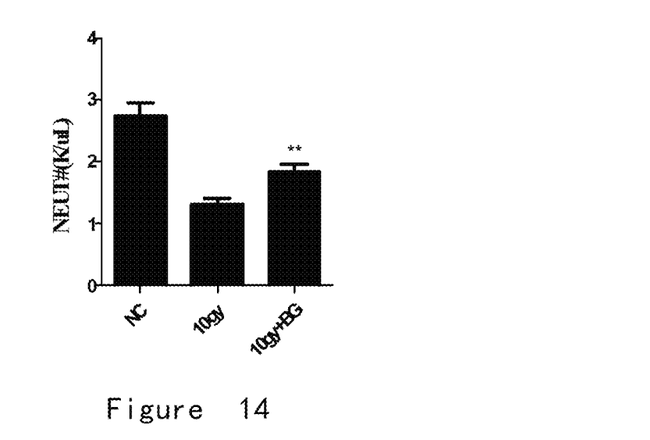
Figure 15:
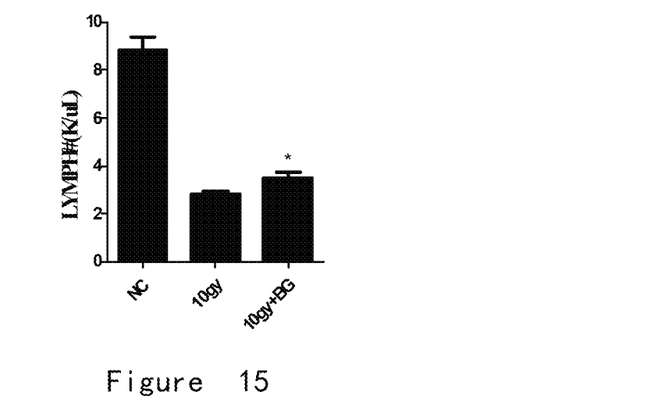

As shown in FIGS. 5-7, radiotherapy significantly inhibits tumor cell growth, and β-1,3/1,6-glucan enhances the anti-tumor effect of radiotherapy.

A cell suspension of $3 \times 10^5$ mouse melanoma cell line B16 (presented by PerkinElmer) was injected subcutaneously into C57BL/6J mice (female, 6-8 weeks old, purchased from Jinan Pengyue Experimental Animal Company)(Overwijk & Restifo, 2001). About 5 days after tumor implantation, local radiotherapy (tumor injection area, 10 Gy) was applied. On day 6 and day 14, vehicle or β-1,3/1,6-glucan was administered (tail vein injection, once a week), and on day 17, after the animals were sacrificed, tumor weight was measured. Blood was taken from the heart after animal sacrificed, placed into EDTA-anticoagulation tubes. After mixing, 50 μl of whole blood was taken and the immune cell concentration was measured by a hematology analyzer.

As shown in FIGS. 8-15, radiotherapy decreases the concentration of immune cells in animals during anti-tumor, which is detrimental to the survival status of mice, while β-1,3/1,6-glucan can be used as an immune stimulant to stimulate immune cells, having the effect of increasing the concentration of immune cells and effectively reducing the side effects of radiotherapy.

On day 14, blood was taken from the heart after animals were sacrificed, and placed in EDTA-anticoagulation tubes. After mixing, 50 μl of whole blood was taken. 5 μl of GFP microspheres were added to each sample for erythrocyte lysis.

The single-cell suspensions were blocked with blocking buffer (20% FBS, 1:100 CD16/CD32 antibody and 1:100 rat IgG) for 20 min, and incubated and staining with the corresponding immune cell surface protein antibodies (CD4-BV510, CD8-PerCP-Cy5.5, CD19-APC) for 30 minutes at 4° C. Analysis of immune cell population ratios was performed by FACS Anal III (BD Biosciences). The specific procedure was delineating the cell population in the FSC/SSC quadrant, delineating the single cell population by FSC-H and FSC-A, and delineating the corresponding immune cells by immune cell surface markers, and calculating the relative immune cell concentration.

Figure 16:
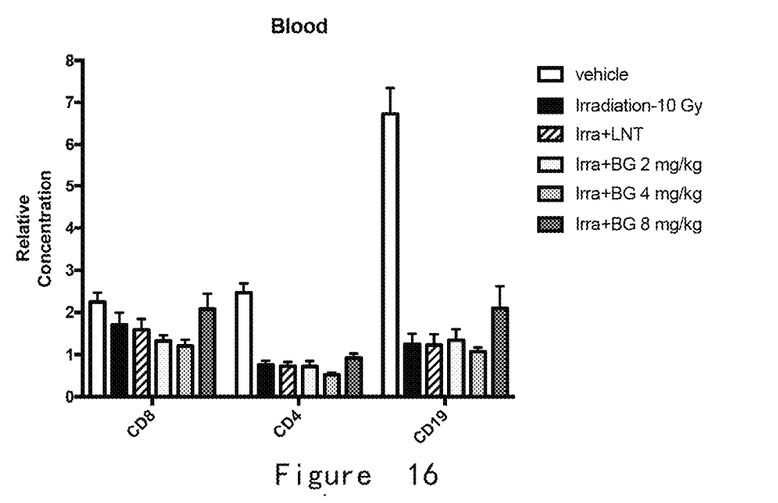
FIG. 16 shows the effect of β-1,3/1,6-glucan in combination with radiotherapy on peripheral blood in the B16 syngeneic tumor model.
Figure 17:
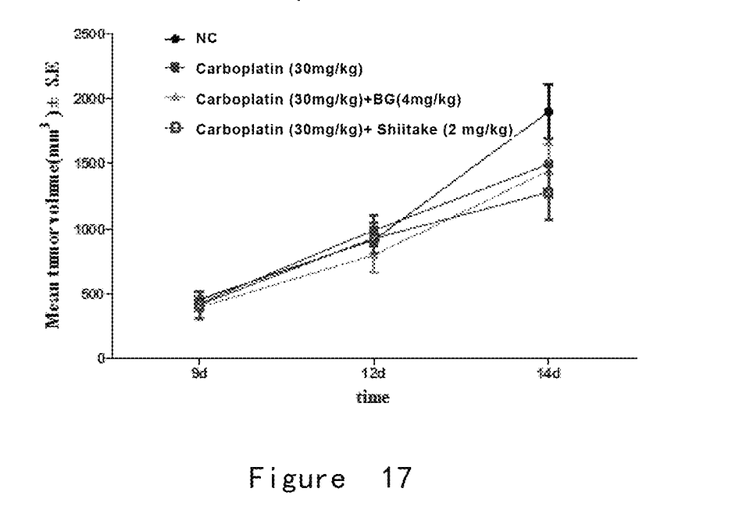
FIGS. 17 to 21 show the effect of β-1,3/1,6-glucan in combination with chemotherapy on the B16 syngeneic tumor model.
Figure 18:
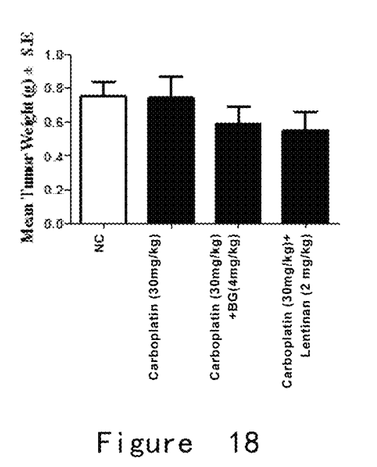
Figure 19:
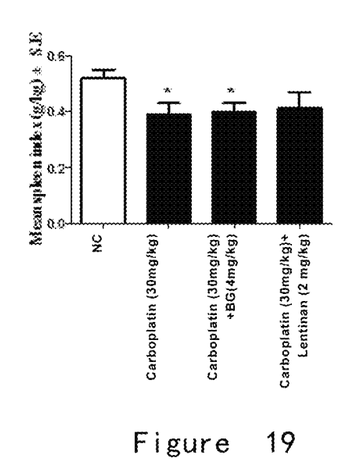
Figure 20:
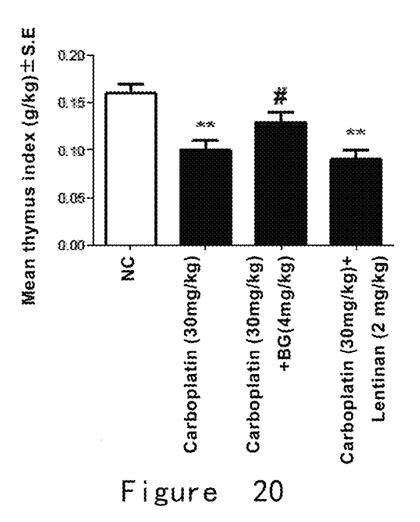
Figure 21:
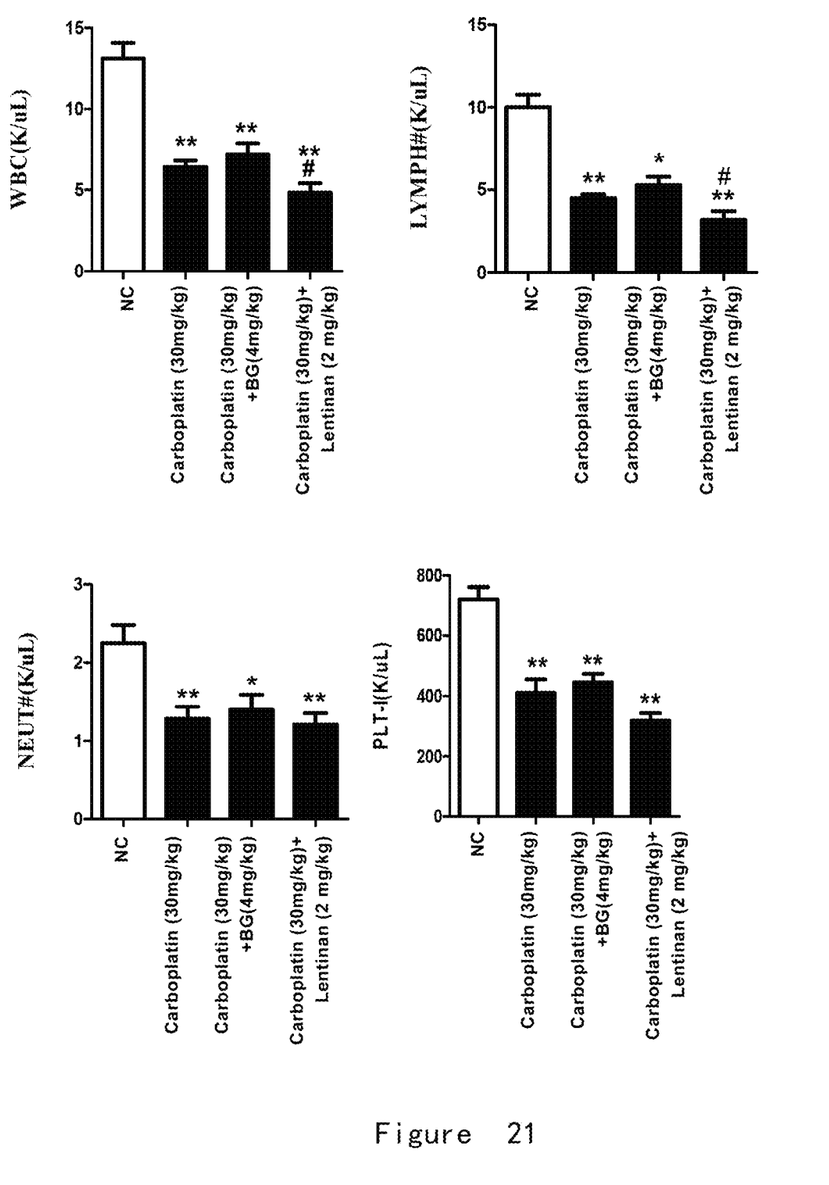

The results in FIG. 16 showed that radiotherapy reduces the cell concentrations of CD4, CD8 and CD19, while 8 mg/kg of β-1,3/1,6-glucan increases the concentration of the corresponding cells, thereby playing a role in stimulation of immune system.

Example 5. β-1,3/1,6-Glucan Combined with Chemotherapy in Mouse Tumor Model

Effects of β-1,3/1,6-glucan combined with chemotherapy on leukocytes and platelets A cell suspension of $3\times10^5$ mouse melanoma cell line B16 (presented by PerkinElmer) was injected subcutaneously into C57BL/6J mice (females, 6-8 weeks old, purchased from Jinan Panyue Experimental Animal Company) (Overwijk & Restifo, 2001). About 2 days after tumor implantation, carboplatin (30 mg/kg, twice a week) was injected intraperitoneally and BG136 (4 mg/kg) or lentinan LNT (2 mg/kg) was injected via the tail vein, and tumor volume were measured during administration, and on day 15, after animals were sacrificed, tumor weight was measured. Blood was taken from the heart after animals were sacrificed, placed in EDTA-anticoagulation tubes. After mixing, 50 μl of whole blood was taken and the immune cell concentration was measured by a hematology analyzer.

As shown in FIGS. 17-21, BG136 enhances the tumor suppressive effect of carboplatin and stimulates the immune response, reverses the immunosuppression after carboplatin administration, as well as the decrease in platelets.

Example 6

Since immune cells play an important role in many types of tumor cell, the antitumor and Leukogenic and platelet-raising effects of β-1,3/1,6-glucan may play a role in various tumor cells (e.g., lung cancer, kidney cancer, liver cancer, breast cancer, etc.).

In addition, immune cells play a regulatory role in tumor metastasis and tumorigenesis, and thus, β-1,3/1,6-glucan may inhibit tumor cell metastasis and tumorigenesis.

All documents referred to in the present invention are incorporated by reference herein as if each document is individually incorporated by reference. Further, it should be understood that upon reading the above teaching of the present invention, various modifications or modifications may be made to the present invention by those skilled in the art, and those equivalents also fall within the scope defined by the appended claims of the present application.

The invention claimed is:

1. A method for treating leukopenia and/or thrombocytopenia, the method comprising a step of administering β-1,3/1,6-glucan in combination with an immune checkpoint drug to a subject in need, wherein the β-1,3/1,6-glucan is derived from Antarctic brown algae; wherein the immune checkpoint drug is a programmed death 1 protein (PD-1) antagonist or a PD-L1 antagonist.

2. The method according to claim 1, wherein the immune checkpoint drug is selected from the group consisting of an anti-PD-1 antibody and an anti-PD-L1 antibody.

3. The method according to claim 2, wherein the anti-PD-1 antibody or PD-L1 antibody is selected from Durvalumab, Atezolizumab, Nivolumab, Spartalizumab, and Camrelizumab, or a combination thereof.

4. The method according to claim 1, wherein the β-1,3/1,6-glucan is can further be administered in combination with at least one chemotherapeutic agent.

5. The method according to claim 4, wherein the at least one chemotherapeutic agent is selected from cytotoxic chemotherapeutic agents.

6. The method according to claim 1, wherein the β-1,3/1,6-glucan is further administered in combination with radiotherapy.

7. The method according to claim 1, wherein the subject in need is a subject with cancer.

8. The method according to claim 7, wherein the cancer is selected from one or more of melanoma, colorectal cancer, lung cancer, kidney cancer, liver cancer and breast cancer.

9. The method according to claim 1, wherein the Antarctic brown algae is selected from Cochayuyo, sea bamboo shoot, *Lessonia trabeculata*, or *Durvillaea antarctica*.

10. The method according to claim 1, wherein the Antarctic brown algae is *Durvillaea antarctica*.

11. The method according to claim 1, wherein the β-1,3/1,6-glucan is a β-glucan of formula (I) and/or formula (II), wherein n is an integer selected from 1-20, and R is H and/or no more than 4 glucose residues.

12. The method according to claim 1, wherein the β-1,3/1,6-glucan has a molecular weight of 1-50 kDa.

13. The method according to claim 1, wherein the thrombocytopenia is a thrombocytopenia caused by the use of the immune checkpoint drug.

* * * * *